(12) United States Patent
Deguchi

(10) Patent No.: US 12,215,357 B2
(45) Date of Patent: Feb. 4, 2025

(54) APPARATUS AND METHOD FOR ESTABLISHMENT OF INDUCED PLURIPOTENT STEM CELLS

(71) Applicants: Canon Medical Systems Corporation, Otawara (JP); Canon Kabushiki Kaisha, Tokyo (JP)

(72) Inventor: Katsuaki Deguchi, Otawara (JP)

(73) Assignees: Canon Medical Systems Corporation, Otawara (JP); Canon Kabushiki Kaisha, Tokyo (JP)

( * ) Notice: Subject to any disclaimer, the term of this patent is extended or adjusted under 35 U.S.C. 154(b) by 226 days.

(21) Appl. No.: 17/503,634

(22) Filed: Oct. 18, 2021

(65) Prior Publication Data

US 2022/0119774 A1   Apr. 21, 2022

(30) Foreign Application Priority Data

Oct. 19, 2020   (JP) ................... 2020-175302

(51) Int. Cl.
    *C12N 5/074*   (2010.01)
    *C12M 1/00*   (2006.01)

(52) U.S. Cl.
    CPC ........... *C12N 5/0696* (2013.01); *C12M 45/06* (2013.01)

(58) Field of Classification Search
    None
    See application file for complete search history.

(56) References Cited

U.S. PATENT DOCUMENTS

| | | | | |
|---|---|---|---|---|
| 4,977,245 A | * | 12/1990 | Jones | C07K 16/24 514/19.3 |
| 6,133,433 A | * | 10/2000 | Pande | C07K 14/005 435/71.1 |
| 10,508,260 B2 | | 12/2019 | Tanabe et al. | |
| 2012/0258459 A1 | * | 10/2012 | Huang | B01L 3/5021 210/767 |
| 2017/0349912 A1 | * | 12/2017 | Borenstein | B01L 3/502746 |

(Continued)

FOREIGN PATENT DOCUMENTS

| | | | | |
|---|---|---|---|---|
| CN | 107884562 B | * | 10/2020 | ............. B01D 29/05 |
| JP | WO 2017/038887 A1 | | 3/2017 | |

(Continued)

OTHER PUBLICATIONS

González, F., Boué, S., & Belmonte, J. C. I. (2011). Methods for making induced pluripotent stem cells: reprogramming a la carte. Nature Reviews Genetics, 12(4), 231-242. (Year: 2011).*

(Continued)

*Primary Examiner* — Evelyn Y Pyla
(74) *Attorney, Agent, or Firm* — Oblon, McClelland, Maier & Neustadt, L.L.P.

(57) ABSTRACT

According to one embodiment, a method for the establishment of an induced pluripotent stem (iPS) cell includes a suspension liquid feeding step, an inducing factor feeding step, and an establishing step. The suspension liquid feeding step feeds a suspension liquid containing a target cell. The inducing factor feeding step feeds an inducing factor to a trap. The trap traps the target cell contained in the suspension liquid fed in the suspension liquid feeding step. The establishing step establishes an iPS cell by introducing the inducing factor, which has been fed to the trap, into the target cell trapped by the trap.

16 Claims, 8 Drawing Sheets

(56) References Cited

U.S. PATENT DOCUMENTS

2019/0338237 A1* 11/2019 Tanabe .................. C12M 29/00
2022/0306981 A1*  9/2022 Tanabe .................. C12M 33/04

FOREIGN PATENT DOCUMENTS

JP      2017-221186 A    12/2017
JP       2019-80575 A     5/2019

OTHER PUBLICATIONS

"Feed, v." OED Online. Oxford University Press, Sep. 2022. Web. Nov. 30, 2022. Retrieved from the internet: < https://www.oed.com/view/Entry/68963?rskey=EUsNnH&result=5#> (Year: 2022).*
ATCC, Peripheral Blood Mononuclear Cells, 7 pages, retrieved from the internet (2024): https://www.atcc.org/cell-products/primary-cells/immune-cells/peripheral-blood-mononuclear-cells#t=productTab&numberOfResults=24 (Year: 2024).*
Mitopedia, PBMC, 1 page, retrieved from the internet (2024): https://www.bioblast.at/index.php/PBMC (Year: 2024).*

* cited by examiner

APPARATUS AND METHOD FOR ESTABLISHMENT OF INDUCED PLURIPOTENT STEM CELLS

CROSS-REFERENCE TO RELATED APPLICATION(S)

This application is based upon and claims the benefit of priority from Japanese Patent Application No. 2020-175302, filed Oct. 19, 2020, the entire contents of which are incorporated herein by reference.

FIELD

Embodiments described herein relate generally to an apparatus and a method for the establishment of induced pluripotent stem (iPS) cells.

BACKGROUND

The establishment of induced pluripotent stem (iPS) cells requires steps of extracting mononuclear cells from blood and adding a factor for turning the extracted mononuclear cells into iPS cells, followed by a step of cultivating the iPS cells. These steps are conducted using large scale installations such as a centrifugal separator in combination with manual operations by engineers.

This establishment method, however, poses a number of problems. First, costs are problematic. Arrangement and maintenance of large scale installations are very expensive. Second, quality is a concern. The series of steps involve complicated and delicate work, and a difference in personal skills in the manual operations could incur variations in qualities of resultant cells. Third, time is consumed. Each of said steps takes several days to complete, and moreover, the establishment of iPS cells is permitted for only one individual per one operation line due to the need to avoid contamination of the cells. As such, in order to prepare iPS cells from many donors, a very long period of time would be required.

DETAILED DESCRIPTION

In general, according to one embodiment, a method for the establishment of an induced pluripotent stem (iPS) cell includes a suspension liquid feeding step, an inducing factor feeding step, and an establishing step. The suspension liquid feeding step feeds a suspension liquid containing a target cell. The inducing factor feeding step feeds an inducing factor to a trap. The trap traps the target cell contained in the suspension liquid fed in the suspension liquid feeding step. The establishing step establishes an iPS cell by introducing the inducing factor, which has been fed to the trap, into the target cell trapped by the trap.

Embodiments of an apparatus and a method for the establishment of iPS cells will be described in detail with reference to the drawings.

Figure 1:
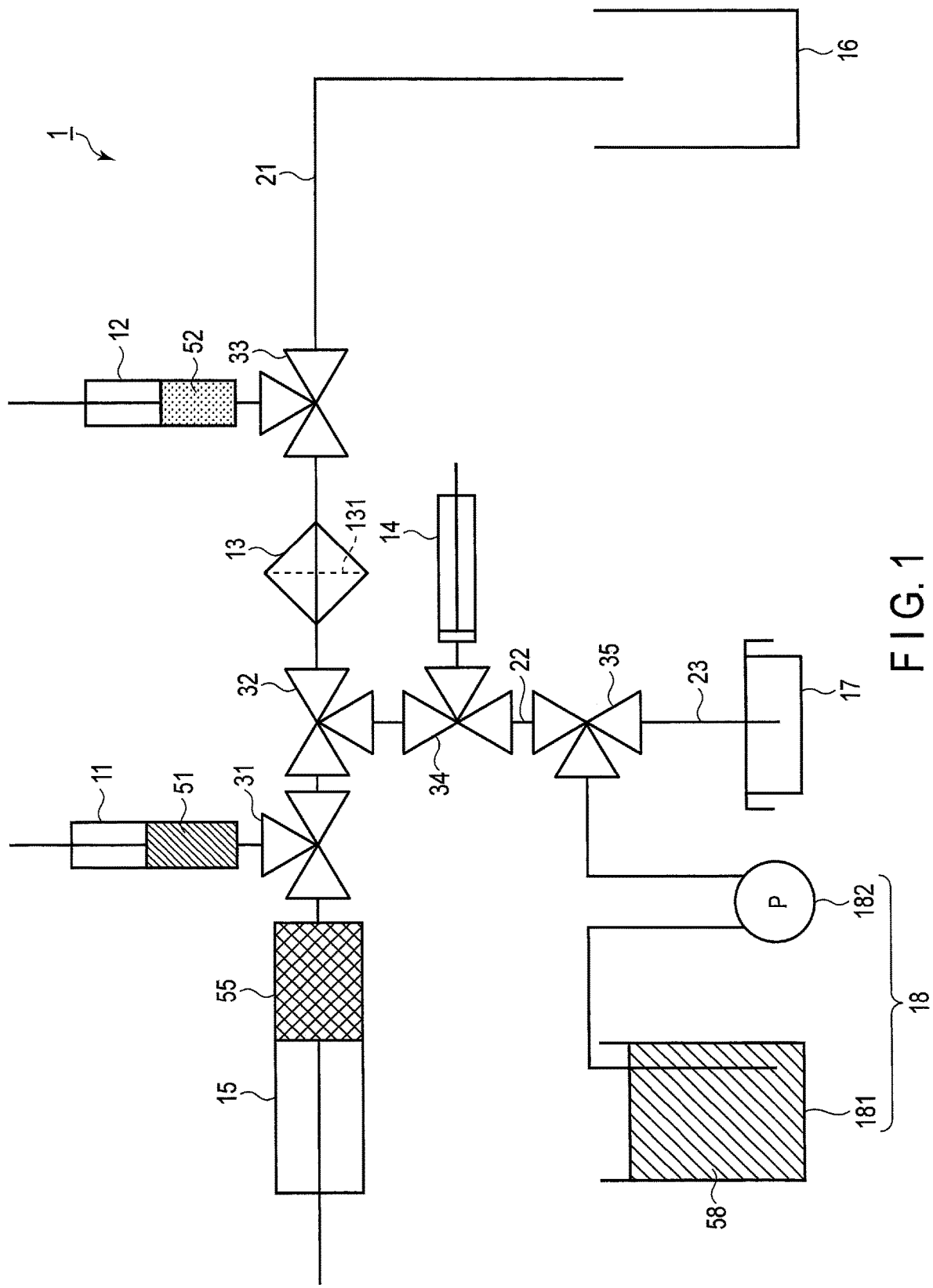
FIG. 1 shows an exemplary configuration of an induced pluripotent stem (iPS) cell establishment apparatus according to an embodiment.

FIG. 1 shows an exemplary configuration of an iPS cell establishment apparatus 1 according to an embodiment. As shown in FIG. 1, the iPS cell establishment apparatus 1 includes a suspension liquid feeder 11, an inducing factor feeder 12, a trap 13, an establisher 14, a wash liquid feeder 15, a waste liquid receiver 16, a cultivator 17, and a culture medium feeder 18.

As shown in FIG. 1, the suspension liquid feeder 11, the inducing factor feeder 12, the trap 13, the establisher 14, the wash liquid feeder 15, the waste liquid receiver 16, the cultivator 17, and the culture medium feeder 18 are each provided in association with a flow channel. In one example, the flow channel includes a first flow channel 21, a second flow channel 22, and a third flow channel 23. As the components associated with the first flow channel 21, the wash liquid feeder 15, the suspension liquid feeder 11, the trap 13, the inducing factor feeder 12, and the waste liquid receiver 16 are arranged in this order in the flow direction (from the upstream side to the downstream side). The first flow channel 21 receives an inflow suspension liquid fed from the suspension liquid feeder 11 and an inflow inducing factor fed from the inducing factor feeder 12. In the first flow channel 21, the suspension liquid flows in a first direction, and the inducing factor flows in a second direction opposite the first direction. The second flow channel 22 is a path branching off from the first flow channel 21 at a position upstream of the trap 13 and has the establisher 14 downstream. Here, the position where the second flow channel 22 branches off is a position on the first flow channel 21 that is between the entrance for the suspension liquid and the trap 13. The third flow channel 23 is coupled with the second flow channel 22 on the downstream side, and has the culture medium feeder 18 upstream and the cultivator 17 downstream.

The suspension liquid feeder 11 feeds a suspension liquid 51 which contains target cells. The suspension liquid 51 may be blood in which target cells extracted from a human body are suspended, or a preservative solution in which the target cells are suspended. The target cells refer to the cells to be reprogrammed by the inducing factor. The target cells may be cells derived from blood or cells of other origin, as long as they are reprogrammable somatic cells. As the blood-derived target cells, mononuclear cells are used.

The suspension liquid feeder 11 is constituted by, for example, an injector including a cylinder and a piston. The cylinder is adapted to contain the suspension liquid 51 with an airtight configuration so that the suspension liquid 51 is inhibited or prevented from being exposed to the ambient air. In this example, the tip of the cylinder is connected to the first flow channel 21 via a valve 31. The piston pushes out the suspension liquid 51 contained in the cylinder.

The inducing factor feeder 12 feeds an inducing-factor-containing culture medium 52 to the trap 13. The inducing-factor-containing culture medium 52 is formed of an inducing factor and a culture medium for establishing iPS cells. The inducing factor is employed for reprogramming the target cells and includes, as concrete examples, one or more of Oct family genes, Klf family genes, Myc family genes, and their respective gene products. In one example, Oct3/4 is used as the Oct family gene, Klf4 is used as the Klf family gene, and c-Myc or L-Myc is used as the Myc family gene. The inducing factor may also include Sox family genes and/or gene products. As the Sox family gene, Sox2 may be used.

The inducing factor feeder 12 is constituted by, for example, an injector including a cylinder and a piston. The cylinder is adapted to contain the inducing-factor-containing culture medium 52 with an airtight configuration so that the culture medium 52 is inhibited or prevented from being exposed to the ambient air. In this example, the tip of this cylinder is connected to the first flow channel 21 via a valve 33. The piston pushes out the culture medium 52 contained in the cylinder.

The trap 13 is arranged at a position on the first flow channel 21 that is between the suspension liquid feeder 11 and the inducing factor feeder 12. In other words, the trap 13 is arranged between the entrance for the suspension liquid and the entrance for the inducing factor, in the middle of the first flow channel 21. The trap 13 traps the target cells contained in the suspension liquid 51 fed from the suspension liquid feeder 11. In one example, the trap 13 is constituted by a container including a filter 131 with meshes that can catch the target cells while permitting other substances having a smaller particle size than the target cells to pass through.

The establisher 14 is connected to the second flow channel 22 so that the target cells and the inducing factor are fed to the establisher 14 through the second flow channel 22. The establisher 14 establishes iPS cells by having the inducing factor that has been fed to the trap 13 introduced into the target cells that have been trapped by the trap 13. The establisher 14 sends the established iPS cells to the cultivator 17.

The establisher 14 is constituted by, for example, an injector including a cylinder and a piston. The cylinder is adapted to contain the inducing-factor-containing culture medium 52 that has been fed from the inducing factor feeder 12 and passed through the trap 13, as well as the target cells that have been trapped by the trap 13. The cylinder has an airtight configuration so that the inducing-factor-containing culture medium 52 and the target cells are inhibited or prevented from being exposed to the ambient air. Also, this cylinder is adapted to contain the iPS cells established by the introduction of the inducing factor into the target cells. In this example, the tip of the cylinder is connected to the second flow channel 22 via a valve 34. The piston pushes out the iPS cells contained in the cylinder.

The wash liquid feeder 15 feeds a wash liquid 55 to the first flow channel 21 so that the trap 13 is washed by the wash liquid 55. The wash liquid 55 is, for example, a saline solution or the like, and a liquid that does very little damage to the target cells may be adopted as the wash liquid 55.

The wash liquid feeder 15 is constituted by, for example, an injector including a cylinder and a piston. The cylinder is adapted to contain the wash liquid 55 with an airtight configuration so that the wash liquid 55 is inhibited or prevented from being exposed to the ambient air. In this example, the tip of the cylinder is connected to the first flow channel 21 via the valve 31. The piston pushes out the wash liquid 55 contained in the cylinder. The waste liquid receiver 16 is a container to receive waste liquid. The waste liquid receiver 16 receives, as the waste liquid, the suspension liquid 51 and the wash liquid 55 that have passed through the trap 13. The waste liquid receiver 16 may be a flask, a bag, or any container that can receive and hold the waste liquid.

The cultivator 17 cultivates the iPS cells established by the establisher 14. The cultivator 17 may be a well plate, a flask, a dish, a bag, or any container that can be used to cultivate iPS cells.

The culture medium feeder 18 feeds a culture medium for cultivating the iPS cells to the cultivator 17. The culture medium feeder 18 includes a culture medium reservoir 181 and a pump 182. The culture medium reservoir 181 is a container to reserve the culture medium. The pump 182 suctions the culture medium from the culture medium reservoir 181 and discharges the suctioned culture medium into the third flow channel 23 so that the culture medium is fed to the cultivator 17.

The first flow channel 21 is provided with multiple valves including the aforementioned valves 31 and 33. The valve 31 is arranged near one end (upstream side) of the first flow channel 21 and connected to the suspension liquid feeder 11 and the wash liquid feeder 15. The valve 31 is adapted to shift between permitting and stopping of the feed of the suspension liquid from the suspension liquid feeder 11 to the first flow channel 21, and also to shift between permitting and stopping of the feed of the wash liquid from the wash liquid feeder 15 to the first flow channel 21. There is a valve 32 at the position on the first flow channel 21 where the second flow channel 22 branches off. The valve 33 is arranged near the other end (downstream side) of the first flow channel 21 and is connected with the inducing factor feeder 12. The valve 33 is adapted to shift between permitting and stopping of the feed of the inducing-factor-containing culture medium 52 to the first flow channel 21. The second flow channel 22 is provided with the aforementioned valve 34. The valve 34 is connected to the establisher 14. The valve 34 is adapted to shift between permitting and stopping of the feed of the inducing-factor-containing culture medium 52 that has passed through the trap 13 and the target cells that have been trapped by the trap 13, to the establisher 14. The third flow channel 23 is provided with a valve 35. The valve 35 is connected to the cultivator 17 and the culture medium feeder 18. The valve 35 is adapted to shift between permitting and stopping of the feed of the established iPS cells from the establisher 14 to the third flow channel 23, and also to shift between permitting and stopping of the feed of the culture medium from the culture medium feeder 18 to the third flow channel 23.

The valves 31 to 35 may each be a two-way valve, a three-way valve, or any type of valve that can open and close the associated channels. As one example, the embodiment will assume each of the valves 31 to 35 to be a three-way valve adapted as a channel switching valve. A three-way valve is a mechanical component constituted by a body element having three openings and a valving element adapted to open two of these openings while closing the remaining one opening. The valving elements in the valves 31 to 35 may each perform channel switching actions under manual and/or electromagnetic control.

The first flow channel 21, the second flow channel 22, and the third flow channel 23 are each constituted by, for example, an airtight flexible tubular member such as a vinyl or plastic tube. Each liquid flowing through the first flow channel 21, the second flow channel 22, and the third flow channel 23 is thus inhibited or prevented from being exposed to the ambient air.

Figure 2:
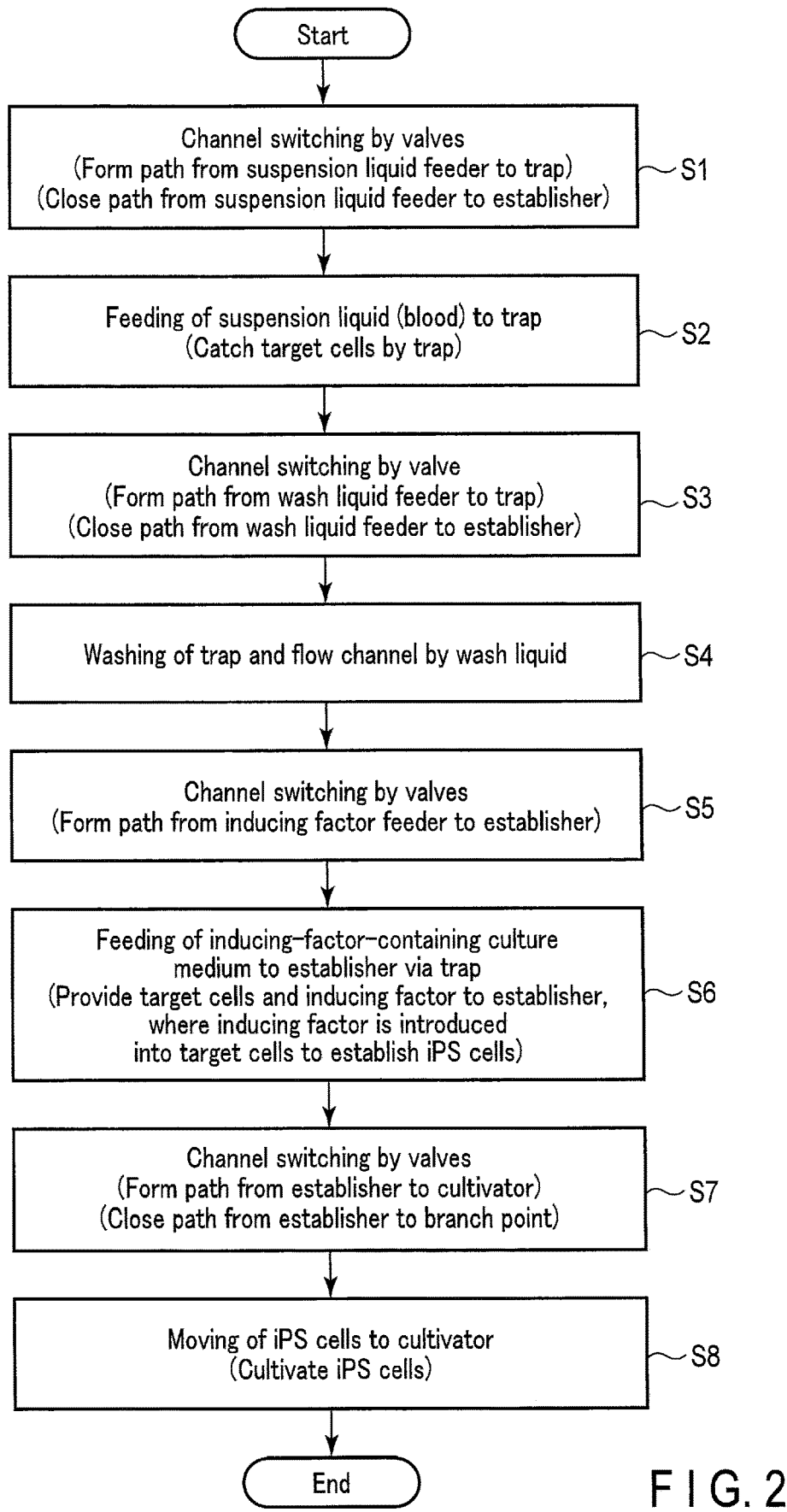
FIG. 2 shows how the establishment and cultivation of iPS cells proceed by use of the iPS cell establishment apparatus.
Figure 3:
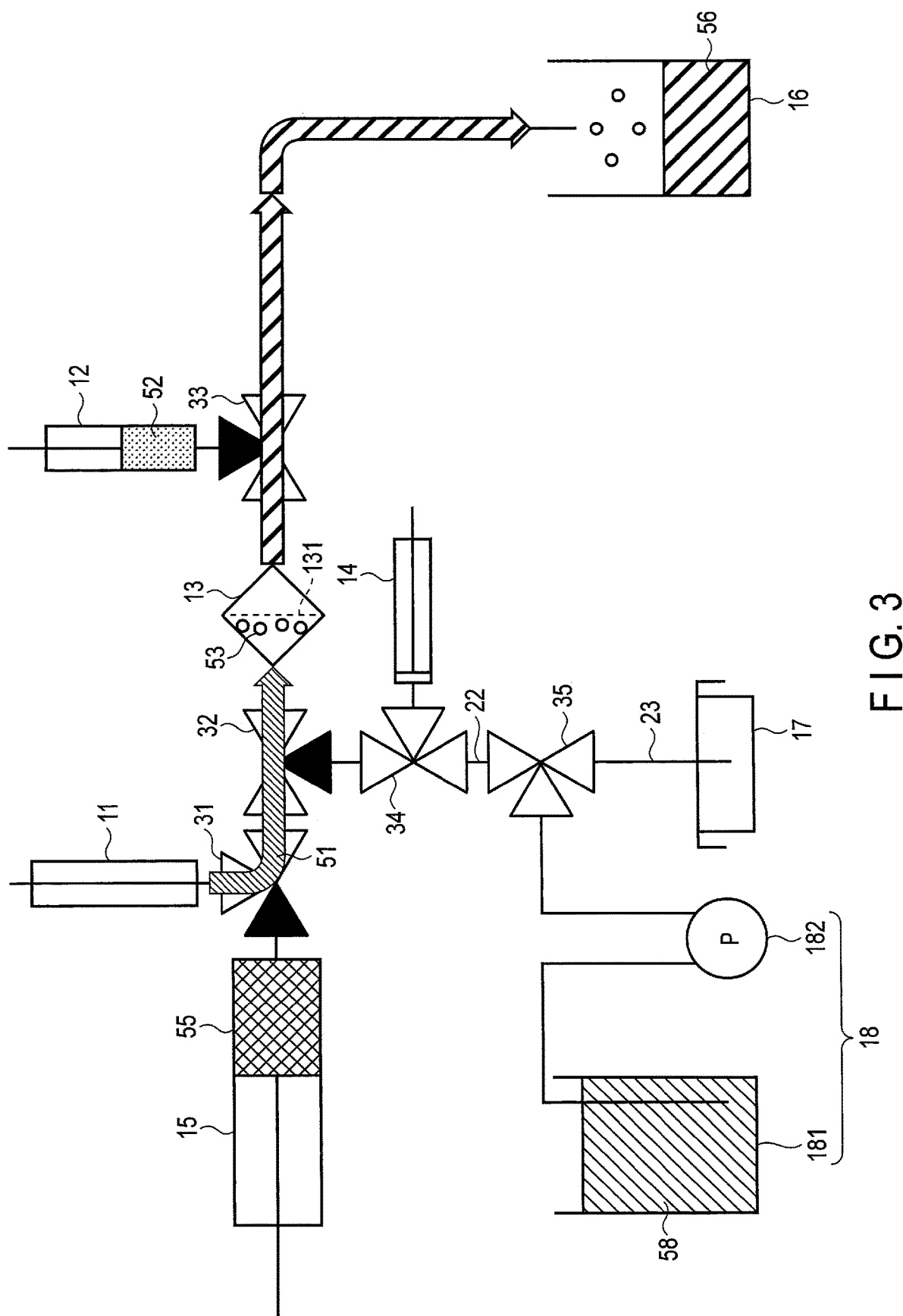
FIG. 3 schematically shows the flow of blood in step S2.
Figure 4:
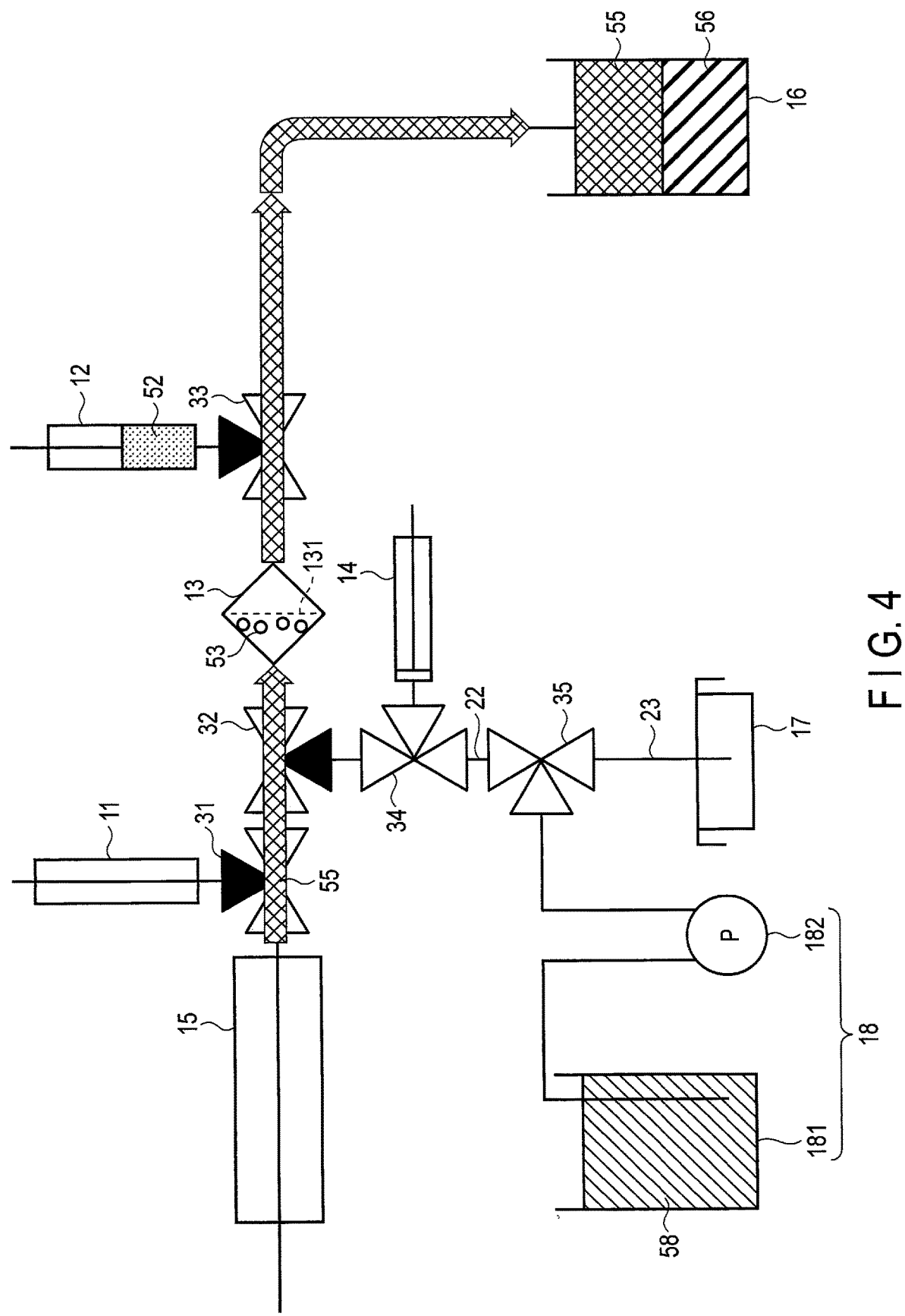
FIG. 4 schematically shows the flow of a wash liquid in step S4.
Figure 5:
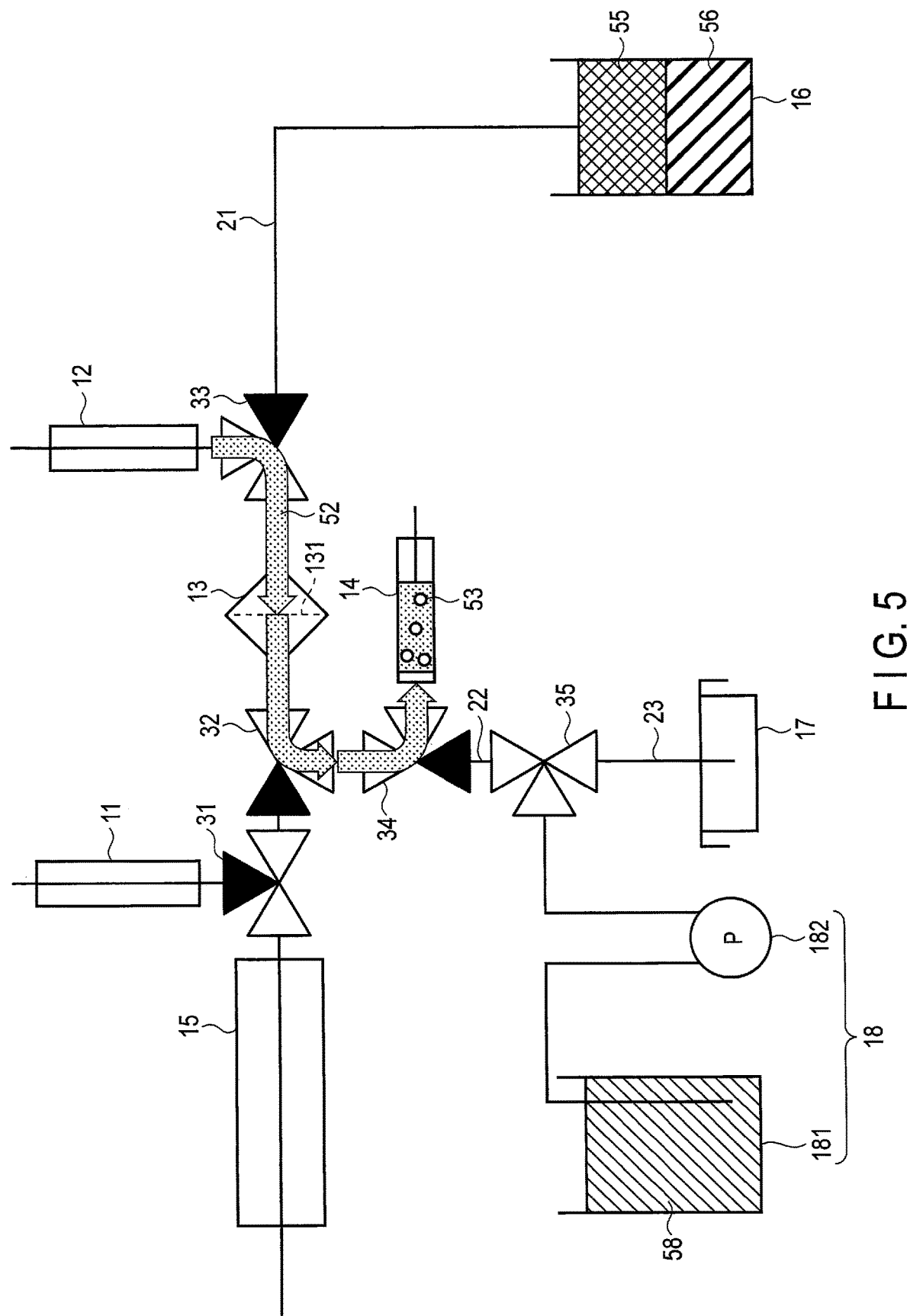
FIG. 5 schematically shows the flow of an inducing-factor-containing culture medium in step S6.
Figure 6:
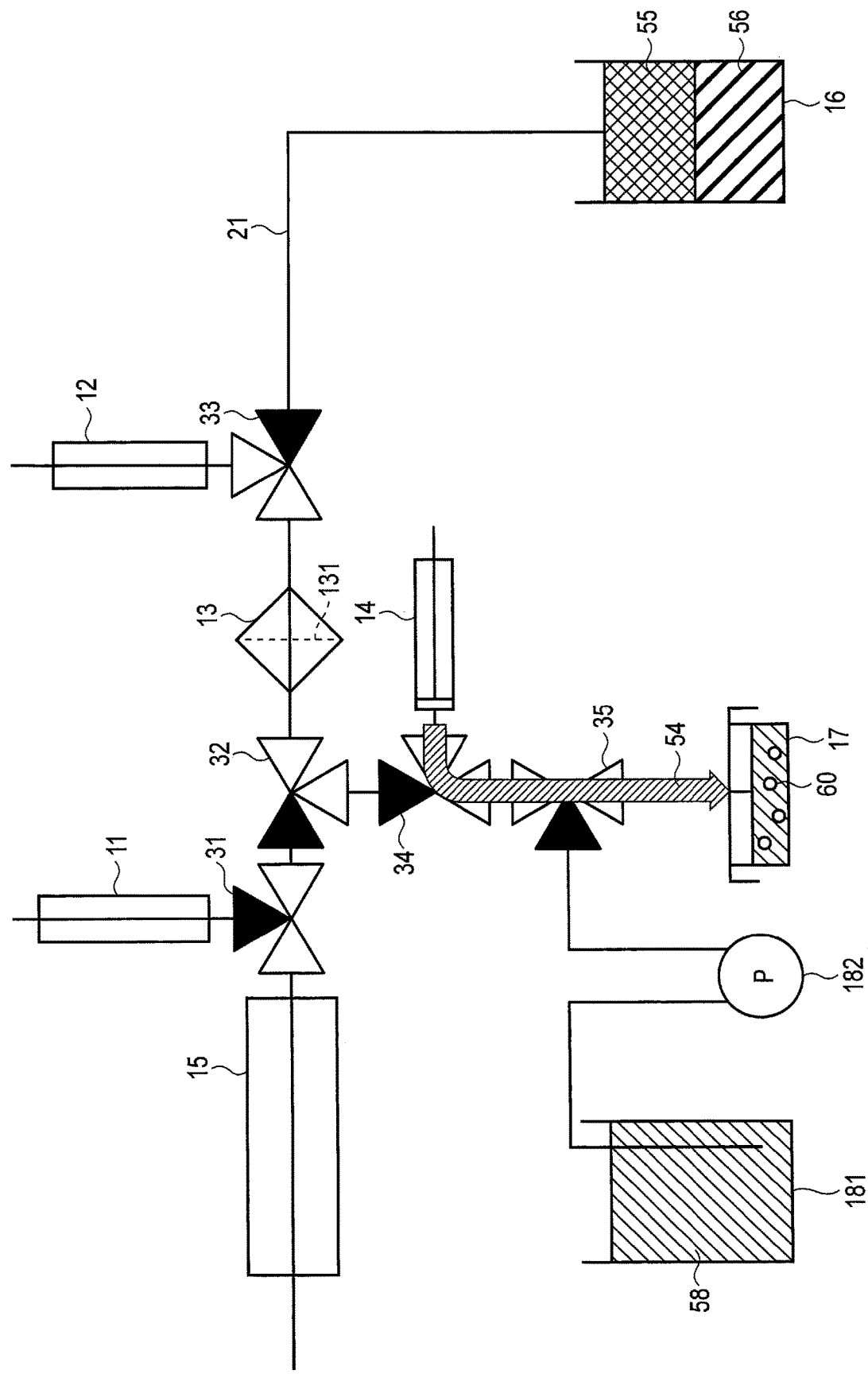
FIG. 6 schematically shows the flow of iPS cells in step S8.

A description will be given of an exemplary operation of the iPS cell establishment apparatus 1 configured as above. FIG. 2 shows how the establishment and cultivation of iPS cells proceed by use of the iPS cell establishment apparatus 1. FIG. 3 relates to step S2 and schematically shows the flow of blood. FIG. 4 relates to step S4 and schematically shows the flow of the wash liquid. FIG. 5 relates to step SG and schematically shows the flow of the inducing-factor-containing culture medium. FIG. 6 relates to step S8 and schematically shows the flow of the iPS cells. Note that the example shown in FIG. 2 assumes that the suspension liquid is blood collected from a donor. It will also be assumed that, at the start of the operation shown in FIG. 2, the suspension liquid feeder 11 retains the blood, the inducing factor feeder 12 retains the inducing-factor-containing culture medium, and the wash liquid feeder 15 retains the wash liquid, each in an amount corresponding to one operation.

As shown in FIG. 2, the channel switching by the valves 31, 32, and 33 is performed first (step S1). More specifically, a path from the suspension liquid feeder 11 to the trap 13 is formed while a path from the suspension liquid feeder 11 to the establisher 14 is closed. For this, an operator or the like operates the valve 31 so that its valving element opens the opening to the suspension liquid feeder 11 (which may also be called a "blood feeding opening") and the opening to the first flow channel 21 (which may also be called a "discharging opening") and closes the opening to the wash liquid feeder 15 (which may also be called a "wash liquid feeding opening"). Also, the operator or the like operates the valve 32 so that its valving element opens the opening to the suspension liquid feeder 11 (which may also be called a "blood and wash liquid feeding opening") and the opening to the trap 13 (which may also be called a "trap side opening") and closes the opening to the establisher 14 (which may also be called an "establisher side opening"). The operator or the like further operates the valve 33 so that its valving element opens the opening to the trap 13 (which may also be called a "trap side opening") and the opening to the waste liquid receiver 16 (which may also be called a "waste liquid feeding opening") and closes the opening to the inducing factor feeder 12 (which may also be called an "inducing factor feeding opening"). Note that if the initial states of the valves already secure the path from the suspension liquid feeder 11 to the trap 13 and the path from the suspension liquid feeder 11 to the establisher 14 is closed, step S1 may be omitted. Also note that the drawings indicate each of the valves 31, 32, 33, 34, and 35 using three triangle symbols, and these triangle symbols represent three respective openings of the three-way valve. Here, a white triangle indicates an opening opened by the corresponding valving element, and a black triangle indicates an opening closed by the corresponding valving element.

After step S1, the suspension liquid 51 (blood) containing target cells 53 is fed to the trap 13 (step S2). In step S2, the suspension liquid feeder 11 feeds the suspension liquid 51 in a forward direction through the first flow channel 21 to the trap 13. The forward direction is defined as a direction in which the suspension liquid 51 flows toward the waste liquid receiver 16. More specifically, the operator or the like operates the suspension liquid feeder 11 so that the suspension liquid 51 retained in the suspension liquid feeder 11 is discharged into the first flow channel 21. The suspension liquid 51 contains the target cells 53 which are required for preparing iPS cells, and in this example, the suspension liquid 51 is retained in the suspension liquid feeder 11 in an amount corresponding to one operation. Thus, all the suspension liquid 51 retained in the suspension liquid feeder 11 may be discharged. The suspension liquid discharged into the first flow channel 21 enters the trap 13. Among the components (substances) contained in the suspension liquid 51 flowing into the trap 13, the components having a particle size larger than the mesh opening of the filter 131 are caught, while the components having a particle size smaller than the mesh opening of the filter 131 are permitted to pass through. The filter 131 here may be a filter with meshes that can catch, for example, components each having a size equivalent to a white blood cell. Each target cell 53, having a particle size larger than the opening of such meshes, is caught by the filter 131. Red blood cells, etc., not handled as target cells in this example, each have a particle size smaller than the mesh opening, and therefore, pass through the filter 131. The blood components that have passed through the trap 13 are received and held by the waste liquid receiver 16 as a part of a waste liquid 56.

After step S2, the channel switching by the valve 31 is performed (step S3). More specifically, a path from the wash liquid feeder 15 to the trap 13 is formed while a path from the wash liquid feeder 15 to the establisher 14 is closed. For this, the operator or the like operates the valve 31 so that its valving element opens the wash liquid feeding opening and the discharging opening and closes the blood feeding opening.

After step S3, the trap 13 is washed by the wash liquid 55 (step S4). In step S4, the wash liquid feeder 15 causes the wash liquid 55 to wash away the components other than the target cells remaining in the first flow channel 21 and the trap 13, into the waste liquid receiver 16. More specifically, the operator or the like in step S4 operates the wash liquid feeder 15 so that the wash liquid 55 retained in the wash liquid feeder 15 is discharged into the first flow channel 21. The wash liquid 55 is retained in the wash liquid feeder 15 in an amount corresponding to one operation, and therefore, all the wash liquid 55 retained in the wash liquid feeder 15 may be discharged. The wash liquid 55 discharged into the first flow channel 21 makes the components other than the target cells remaining in the first flow channel 21 and the trap 13 flow into the waste liquid receiver 16. In one example, components such as plasma, red blood cells, and platelets mainly constitute the unwanted blood components. Here, by adopting a configuration of advancing and retracting the piston in the wash liquid feeder 15 to repeat the discharge and suction of the wash liquid 55, it is possible to efficiently remove and sweep away the unwanted blood components that stick to the first flow channel 21 or the trap 13. Further, the iPS cell establishment apparatus 1 may be adapted to incline itself in conjunction with the discharge and suction of the wash liquid 55 so that the unwanted blood component can be efficiently washed away.

After step S4, the channel switching by the valves 32, 33, and 34 is performed (step S5). More specifically, a path from the inducing factor feeder 12 to the establisher 14 is formed. For this, the operator or the like operates the valve 32 so that its valving element opens the opening to the trap 13 and the opening to the establisher 14 and closes the opening to the wash liquid feeder 15. Also, the operator or the like operates the valve 33 so that its valving element opens the opening to the inducing factor feeder 12 and the opening to the trap 13 and closes the waste liquid feeding opening. Together, the operator or the like operates the valve 34 so that its valving element opens the opening to the valve 32 (which may also be called a "branch valve side opening") and the opening to the establisher 14 (which may also be called an "establisher side opening") and closes the opening to the cultivator 17 (which may also be called a "cultivator side opening").

After step S5, the inducing-factor-containing culture medium 52 is fed to the establisher 14 via the trap 13 (step S6). In step S6, the inducing factor feeder 12 feeds the inducing-factor-containing culture medium 52 in the direction opposite the forward direction through the first flow channel 21 to the trap 13, so that the inducing-factor-containing culture medium 52 together with the target cells 53 are fed to the establisher 14 via the second flow channel 22. More specifically, the operator or the like in step S6 operates the inducing factor feeder 12 to discharge the inducing-factor-containing culture medium 52 retained in the inducing factor feeder 12 into the first flow channel 21. The inducing-factor-containing culture medium 52 is retained in the inducing factor feeder 12 in an amount corresponding to one operation, and therefore, all the inducing-factor-containing culture medium 52 retained in the inducing factor feeder 12 may be discharged. The discharged inducing-factor-containing culture medium 52 flows into the trap 13 from the direction opposite the flow direction of the suspension liquid 51 in step S2. The inducing-factor-containing culture medium 52 that has entered the trap 13 passes through the filter 131 and flows, together with the target cells 53 caught by the filter 131, into the establisher 14 via the second flow channel 22. Note that the piston in the establisher 14 may be pulled to the limit beforehand in order to accommodate the inducing-factor-containing culture medium 52 and the target cells 53.

In the establisher 14, the inducing factor is introduced into the target cells 53 and iPS cells 60 are established from the target cells. The inducing factor may be provided in a variety of forms. For example, the inducing factor may be integrated into vectors and provided. The vectors here are not limited, and viral vectors such as a Sendai virus vector and a retroviral vector, or non-viral vectors such as a plasmid may be suitably adopted. In an example where an inducing factor-integrated Sendai virus vector is used, the Sendai virus vector and the target cell are brought into contact with each other so that the inducing factor is introduced into this target cell. A gene product of the inducing factor is then generated. The gene product induces the reprogramming of the target cell, thereby giving birth to an iPS cell which is an undifferentiated cell having a pluripotency and a proliferating ability. The thus obtained iPS cells are left to grow under the presence of the culture medium for approximately an hour. In this manner, the iPS cells 60 are established. During the establishing process, the establisher 14 may be suitably maintained at approximately 37° C. and 5% $CO_2$.

For the purpose of enhancing the accuracy of iPS cell establishment in the establisher 14, a container of a relatively small capacity may be suitably used as the cylinder of the establisher 14. This can increase the likelihood of the target cells and the inducing factor, or the inducing factor-integrated vector, contacting each other and, accordingly, increase the likelihood of the iPS cells being successfully established.

After step S6, the channel switching by the valves 34 and 35 is performed (step S7). More specifically, a path from the establisher 14 to the cultivator 17 is formed. For this, the operator or the like operates the valve 34 so that its valving element opens the establisher side opening and the cultivator side opening and closes the branch valve side opening. Together, the operator or the like operates the valve 35 so that its valving element opens the opening to the valve 34 (which may also be called an "establisher side opening") and the opening to the cultivator 17 (which may also be called a "cultivator side opening") and closes the opening to the culture medium feeder 18 (which may also be called a "culture medium feeding opening").

After step S7, the iPS cells 60 are moved to the cultivator 17 (step S8). More specifically, the operator or the like in step S7 operates the establisher 14 so that the a suspension liquid 54, in which the iPS cells 60 are suspended, is discharged from the establisher 14 into the second flow channel 22. The iPS cell suspension liquid 54 discharged into the second flow channel 22 moves to the cultivator 17. The iPS cells 60 that have been moved to the cultivator 17 are cultivated there. During the cultivating process, the cultivator 17 may be suitably maintained at a room temperature of approximately 37° C. For cultivation, a culture medium 58 may be provided from the culture medium feeder 18 suitably and as needed. For example, the operator or the like may operate the valve 35 so that its valving element opens the culture medium feeding opening and the cultivator side opening and closes the establisher side opening, and operate the pump 182 so that an appropriate amount of the culture medium 58 is fed from the culture medium reservoir 181 to the cultivator 17.

In order to have the iPS cells 60 settle in the cultivator 17, a coating agent may be applied to the cultivator 17 prior to step S8. As a concrete example, the cultivator 17 when constituted by a culture dish is applied with a coating agent at its inner bottom. The coating agent is preferably made of cell adhesion molecules such as laminin protein, vitronectin, etc. The cultivator 17 can thus form a scaffold for the iPS cells 60 fed from the establisher 14 and allows the stable cultivation of the iPS cells 60.

Note that the coating agent is not required to be applied to the cultivator 17 in advance. For example, the operator or the like may provide the coating agent to the cultivator 17 using an injector at the time of feeding the iPS cells 60 from the establisher 14 to the cultivator 17. The coating agent may be provided concurrently with, prior to, or after feeding the iPS cells 60 from the establisher 14 to the cultivator 17.

The IPS cell, establishment apparatus 1 may be constructed so that a unit including the suspension liquid feeder 11, the inducing factor feeder 12, and the establisher 14 and a unit including the cultivator 17 and the culture medium feeder 18 can be detached from each other. With this structure, the unit including the suspension liquid feeder 11, the inducing factor feeder 12, and the establisher 14 can be separated from the unit including the cultivator 17 and the culture medium feeder 18 when the movement of the iPS cells 60 to the cultivator 17 is done. For example, the second flow channel 22 may be pulled out from the valve 35 so that a cultivating system including the cultivator 17 and the culture medium feeder 18 coupled via the third flow channel 23 is actualized. That is, by detaching the unit including the cultivator 17 and the culture medium feeder 18 from the other components of the iPS cell establishment apparatus 1, the cultivation of the iPS cells 60 is enabled to proceed using a smaller site.

In the manner as described above, the establishment and cultivation of iPS cells by use of the iPS cell establishment apparatus 1 are completed.

Next, the accuracy of blood component separation by the trap 13 according to the embodiment will be described.

Figure 7:
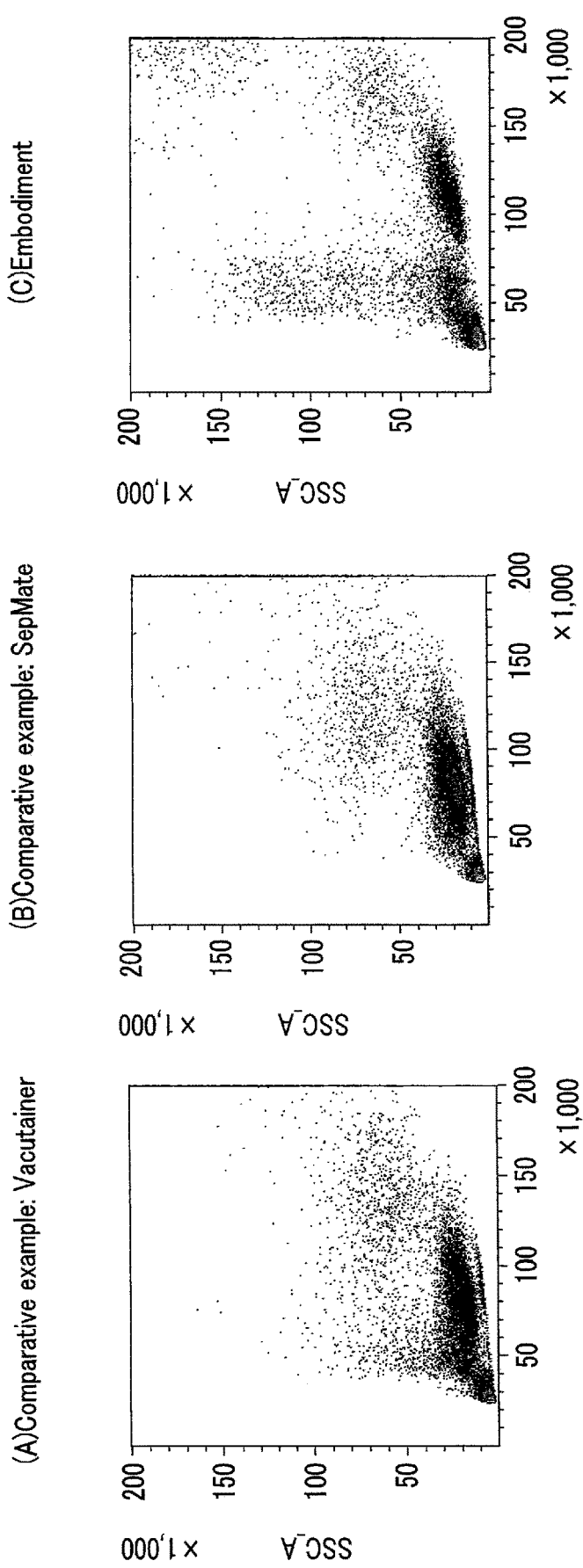
FIG. 7 shows the results of flow cytometry with a flow cytometer for comparative examples and the embodiment.

FIG. 7 shows the results of flow cytometry with a flow cytometer for comparative examples and the embodiment. The comparative examples here adopted the method of separating blood components according to the common density-gradient centrifugation technique. Specifically, for comparative example (A), the figure shows the result of flow cytometry of separated blood cells obtained by subjecting blood contained in a BD Vacutainer (a blood collection tube available from Becton, Dickinson and Company) to separation in the density-gradient centrifugation process. For comparative example (B), the figure shows the result of flow cytometry of separated blood cells obtained by subjecting blood contained in a SepMate (a tube exclusively used for the density-gradient centrifugation technique and available from Veritas Corporation) to separation in the density-gradient centrifugation process. For the embodiment, the figure shows the result of flow cytometry of blood components (separated blood cells) caught by the filter 131 of the trap 13 as described above.

Each measurement result shown in FIG. 7 is expressed in a dot-plotting manner with the vertical axis representing back scatter (SSC) signals and the horizontal axis representing forward scatter (FSC) signals. The SSC signals have a correlation with the complexity of internal structures of the cells, and the FSC signals have a correlation with the size of the cells. As can be understood from the results of the embodiment and the comparative examples in comparison with one another, the filter 131 according to the embodiment has proven to be capable of providing a separation accuracy comparable with that of each comparative example. It has also been confirmed by the present inventor that the use of the iPS cell establishment apparatus 1 enabled the successful establishment of iPS cells having morphometric characteristics and a proliferating ability.

The configuration, etc. of the iPS cell establishment apparatus 1 described above are only examples, and they may be modified in various ways.

(Modification 1)

The foregoing embodiment has assumed a configuration in which the target cells and the inducing-factor-containing culture medium flow into the establisher 14 and the iPS cells are established from the target cells in the establisher 14. The iPS cell establishment apparatus 1 according to this Modification 1 includes a component corresponding to the combination of the trap 13 and the establisher 14.

Figure 8:
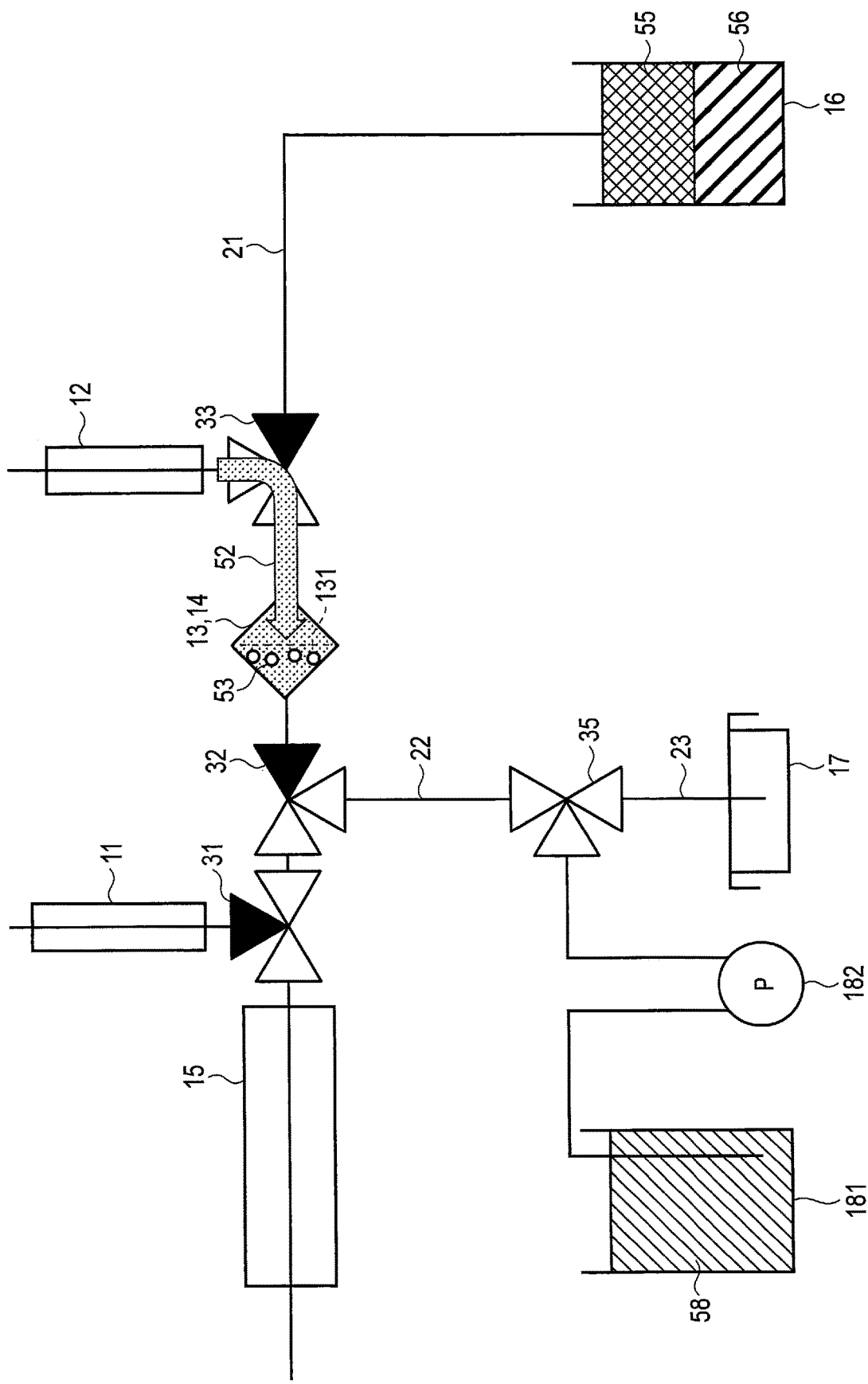
FIG. 8 schematically shows the flow of an inducing-factor-containing culture medium according to Modification 1.

FIG. 8 schematically shows the flow of the inducing-factor-containing culture medium according to Modification 1. As shown in FIG. 8, after step S4 in FIG. 2, a path from the inducing factor feeder 12 to the trap 13 is formed while a path from the trap 13 to the cultivator 17 is closed. For this, the operator or the like operates the valve 32 so that its valving element opens the wash liquid feeding opening and the opening to the valve 35 and closes the trap side opening. Together, the operator or the like operates the valve 33 so that its valving element opens the inducing factor feeding opening and the trap side opening and closes the waste liquid feeding opening.

Next, the operator or the like operates the inducing factor feeder 12 to discharge the inducing-factor-containing culture medium 52 retained in the inducing factor feeder 12 into the first flow channel 21. The discharged inducing-factor-containing culture medium 52 flows into the trap 13 from the direction opposite the flow direction of blood in step S2. The inducing-factor-containing culture medium 52 is stopped and held in the trap 13. Any means may be employed for stopping and holding the inducing-factor-containing culture medium 52. For example, the operator or the like may plug the opening of the trap 13 that opens toward the valve 32 using a stopper, etc., or close the first flow channel 21 at a position between the trap 13 and the valve 32 using a clip, etc. In the trap 13, the inducing factor is introduced into target cells and iPS cells are established from the target cells. After the establishment of the iPS cells in the trap 13, the iPS cell suspension liquid is moved to the cultivator 17.

According to Modification 1, it is possible to provide the trap 13 and the establisher 14 as a single container. Therefore, the iPS cell establishment apparatus 1 can be realized with a simpler constitution.

(Modification 2)

The foregoing embodiment, etc. have assumed that blood collected from a donor is set in the suspension liquid feeder 11. According to Modification 2, what is set in the suspension liquid feeder 11 is a preservative solution in which target cells are suspended. For example, such a target-cell-suspended preservative solution may be prepared by suspending the target cells trapped by the trap 13 in step S2 or S4 in a preservative solution.

In order to prepare the target-cell-suspended preservative solution, a preservative solution feeder adapted to retain the preservative solution may be coupled with the first flow channel 21 in place of, or additionally in an arrangement similar to, the inducing factor feeder 12. With this configuration, the preservative solution may be fed from the preservative solution feeder to the trap 13 as in step S6. The preservative solution fed to the trap 13 flows into the establisher 14 together with the target cells trapped by the trap 13. In this case, the establisher 14 holds the preservative solution in which the target cells are suspended (the target-cell-suspended preservative solution). The target-cell-suspended preservative solution held in the establisher 14 may be suitably provided to and retained in the suspension liquid feeder 11. The target-cell-suspended preservative solution, as compared to blood, may be preferably adopted for the storage of target cells.

The suspension liquid feeder 11 retaining the target-cell-suspended preservative solution may be used in a manner similar to the suspension liquid feeder 11 retaining blood. More specifically, in step S2, the target-cell-suspended preservative solution is fed to the trap 13 from the suspension liquid feeder 11, and the target cells in the target-cell-suspended preservative solution are trapped by the trap 13. The inducing-factor-containing culture medium is then fed to the trap 13 from the inducing factor feeder 12. The target cells flow into the establisher 14 together with the inducing-factor-containing culture medium so that iPS cells are established from the target cells in the establisher 14. Note that, as in the foregoing embodiment, etc., each target cell trapped by the trap 13 in the modification may be of a size equivalent to a white blood cell.

According to Modification 2, the target cells contained in the preservative solution can also be trapped by the trap 13. Thus, the iPS cell establishment apparatus 1 can be realized with enhanced convenience. Moreover, the iPS cell establishment apparatus 1 can be utilized for preparing target-cell-suspended preservative solutions.

(Modification 3)

According to Modification 3, the trap 13 is also adapted for cultivation of the target cells trapped in step S2. For example, in the trap 13, target cells are caught in step S2 and washing is performed in step S4. Subsequently, a culture medium for cultivating the target cells is fed to the trap 13 so that the target cells are cultivated there.

The culture medium for cultivating the target cells may be provided to the trap 13 by any method. For example, the operator or the like may directly feed the culture medium into the trap 13. As another method, a culture medium feeder adapted to retain the culture medium for cultivating the target cells may be provided additionally or in place of one of the suspension liquid feeder 11, the inducing factor feeder 12, and the wash liquid feeder 15, so that the culture medium is fed to the trap 13 from this culture medium feeder.

Modification 3 enables proliferation of the target cells that serve as materials of iPS cells, and therefore, allows for the establishment of a large amount of iPS cells.

(Modification 4)

The foregoing embodiment, etc. have assumed that the suspension liquid feeder 11, the inducing factor feeder 12, the establisher 14, and the wash liquid feeder 15 are each constituted by a cylinder and a piston, and that the piston may be advanced and retracted manually. Each piston may instead be adapted so that automatic and mechanical advancing and retracting movement can be performed. For example, the suspension liquid feeder 11, the inducing factor feeder 12, the establisher 14, and/or the wash liquid feeder 15 may each be constituted by an electric cylinder capable of pushing and pulling the corresponding piston. More specifically, components of such an electric cylinder may include a cylinder, a piston, and a motor. The piston is supported by a linear motion mechanism that enables sliding movement within the cylinder. The linear motion mechanism is connected to the motor so that it pushes and pulls the piston according to the driven motor. The motor, in response to a "feed" button being pressed, actuates the linear motion mechanism to push forward the piston, whereby the suspension liquid, the inducing-factor-containing culture medium, the iPS cell suspension liquid, or the wash liquid retained in the cylinder is discharged.

The motor of the electric cylinder may also actuate the linear motion mechanism to push the piston in response to the elapse of a predetermined time. In this case, the electric cylinder may include a processor to count the time from a reference time. For example, when the establisher 14 is constituted by such an electric cylinder, the processor counts the time from a reference time and detects that the elapsed time has exceeded a cultivation time (e.g., one hour). The reference time may be suitably set to, for example, the time at which the discharge of the inducing-factor-containing culture medium from the inducing factor feeder 12 is completed, or the time at which the entry of the inducing-factor-containing culture medium and the target cells into the establisher 14 is completed. Then, the processor may drive the motor to push the piston via the linear motion mechanism in response to the elapsed time exceeding the cultivation time. In this manner, the iPS cell suspension liquid can be automatically moved to the cultivator 17. It is known that the amount of each component of blood per unit quantity can vary among different donors. It is also known that, even in the same donor, the amount of blood component varies depending on her/his physical condition, etc. For the strict setting of the cultivation time in the establisher 14, the numbers, etc., of the respective blood components including white cells may be suitably referred to.

(Modification 5)

According to Modification 5, the establisher 14 may be adapted to perform electroporation to introduce the inducing factor into target cells. In one example, the cylinder of the establisher 14 is provided with a pair of electrodes connected to a power unit. The power unit, in response to an instruction input from the operator or the like, or in response to the completion of discharge of the inducing-factor-containing culture medium from the inducing factor feeder 12 or the completion of entry of the inducing-factor-containing culture medium and the target cells into the establisher 14, causes the pair of electrodes to apply electric pulses therebetween. The target cells within the cylinder receive the electric pulse application and form micropores in their cell membranes. Accordingly, the inducing factor or the inducing factor-integrated vectors are introduced through these micropores.

Modification 5 utilizes the electroporation to introduce the inducing factor into target cells, and as such, the inducing factor can be efficiently introduced into the target cells as compared to the cases of the foregoing embodiment, etc. where the electroporation is not performed. Consequently, iPS cells can be established with an enhanced efficiency.

(Modification 6)

The foregoing embodiment, etc. have assumed that each of the valves 31, 32, 33, 34, and/or 35 is a three-way valve, but they may be a two-way valve such as a pinch valve, a gate valve, a ball valve, or a diaphragm valve. The two-way valve may perform channel switching actions under manual and/or electromagnetic control.

(Modification 7)

The foregoing embodiment, etc. have assumed that the suspension liquid feeder 11, the inducing factor feeder 12, the establisher 14, and the wash liquid feeder 15 are each constituted by a cylinder and a piston, and that the piston may be advanced and retracted by hand or automatically. The suspension liquid feeder 11, the inducing factor feeder 12, the establisher 14, and/or the wash liquid feeder 15 may each instead be constituted by a flexible container. Suitable examples of such a container include a bag made of plastic or vinyl materials and having a connector part to connect with the tube forming the associated channel. With this constitution, the operator or the like can grasp the bag so that the target cell suspension liquid, the inducing-factor-containing culture medium, the iPS cell suspension liquid, the wash liquid, or other corresponding liquid is suitably discharged.

(Modification 8)

The foregoing embodiment, etc. have assumed that a coating agent is applied to the cultivator 17. However, this does not pose any limitations to the embodiment, etc. In order to have the target cells settle in the establisher 14, a coating agent may be applied to the establisher 14 prior to step S6. As a concrete example, the establisher 14 when constituted by a culture dish is applied with a coating agent at its inner bottom. The establisher 14 can thus form a scaffold for the target cells fed from the trap 13 and allows the stable establishment of iPS cells.

Note that the coating agent is not required to be applied to the establisher 14 in advance. For example, the operator or the like may provide the coating agent to the establisher 14 using an injector at the time of feeding the target cell suspension liquid and the inducing-factor-containing culture medium from the trap 13 to the establisher 14. The coating agent may be provided concurrently with, prior to, or after feeding the target cell suspension liquid and the inducing-factor-containing culture medium from the trap 13 to the establisher 14. The coating agent provided to the establisher 14 may be transferred from the establisher 14 to the cultivator 17 in step S8.

As another example, the inducing factor feeder 12 may be adapted to retain the coating agent so that the establisher 14 is provided with the coating agent. In this case, the inducing factor feeder 12 may retain the mixture of the inducing-factor-containing culture medium and the coating agent. In step S6, this mixture of the inducing-factor-containing culture medium and the coating agent is fed from the inducing factor feeder 12 to the trap 13, passes through the filter 131, and enters the establisher 14 together with the target cells. The coating agent is thus provided to the establisher 14. The establisher 14 forms a scaffold for the target cells fed from the trap 13 and allows the stable establishment of iPS cells.

Note that the coating agent is not required to be retained in the inducing factor feeder 12. For example, the operator or the like may provide the coating agent to the trap 13 using another injector at the time of feeding the inducing-factorcontaining culture medium from the inducing factor feeder 12 to the trap 13. The coating agent may be provided concurrently with, prior to, or after feeding the inducing-factor-containing culture medium from the inducing factor feeder 12 to the trap 13. As another option, the coating agent may be retained in the empty inducing factor feeder 12 after discharging and feeding the inducing-factor-containing culture medium, so that the coating agent is provided from the inducing factor feeder 12 to the trap 13. Conversely, the inducing factor feeder 12 may first retain only the coating agent, and after the coating agent is provided to the trap 13, the empty inducing factor feeder 12 may retain the inducing-factor-containing culture medium so that the inducing-factor-containing culture medium is subsequently provided from the inducing factor feeder 12 to the trap 13. The coating agent provided to the trap 13 may be transferred from the trap 13 to the establisher 14 in step S6, and then transferred from the establisher 14 to the cultivator 17 in step S8.

(Modification 9)

According to Modification 9, the trap 13 may include a first filter having a first mesh and a second filter having a second mesh. The first mesh catches a substance having a first particle size larger than the target cell and permits a substance having a particle size smaller than the first particle size to pass through. The second mesh catches a substance that has passed through the first mesh and has a second particle size equivalent to the size of the target cell, and permits a substance having a particle size smaller than the second particle size to pass through. In the trap 13, the first filter and the second filter are arranged in this order from the upstream side toward the downstream side. The first filter and the second filter are spaced apart from each other. The target cells are collected in this space.

The trap 13 according to Modification 9 receives the inducing-factor-containing culture medium from the inducing factor feeder 12, as in the foregoing embodiment, etc. The inducing-factor-containing culture medium passes through the second mesh of the second filter and reaches the space between the first filter and the second filter. The inducing-factor-containing culture medium then passes through the first mesh of the first filter together with the target cells present in the space so that the inducing-factor-containing culture medium and the target cells will be fed to the establisher 14 via the second flow channel 22. When the inducing-factor-containing culture medium and the target cells need to be inhibited from flowing into the upstream side (regions of the suspension liquid feeder 11 and the wash liquid feeder 15) beyond the first mesh of the first filter, the upstream side opening of the trap 13 may be discretionarily closed. Or, an opening and closing mechanism may be provided to selectively open and close the mesh openings of the first filter. Such an opening and closing mechanism may have an electrically or mechanically controllable configuration. With this mechanism, at the time of feeding the suspension liquid from the suspension liquid feeder 11, the mesh openings of the first filter are opened so that substances having a particle size smaller than the first particle size (which is larger than each target cell) pass through the first filter. At the time of feeding the inducing-factor-containing culture medium from the inducing factor feeder 12, the mesh openings of the first filter are closed so that the inducing-factor-containing culture medium and the target cells are inhibited from flowing into the upstream side (regions of the suspension liquid feeder 11 and the wash liquid feeder 15) beyond the first mesh of the first filter.

In the trap 13 according to Modification 9, the space between the first filter and the second filter may be connected to a branch channel from the second flow channel 22 and also another flow channel (which will be called a "fifth flow channel"). As such, in the trap 13, the first flow channel 21 crosses the flow channel constituted by the branch of the second flow channel 22 and the fifth flow channel. The fifth flow channel here is connected to the inducing factor feeder 12, and accordingly, the connection between the inducing factor feeder 12 and the first flow channel 21 downstream of the trap 13 is omitted. That is, the flow channel for the inducing-factor-containing culture medium to flow from the inducing factor feeder 12 and the flow channel for the inducing-factor-containing culture medium and the target cells to flow into the establisher 14 may be coupled with each other. Thus, the inducing-factor-containing culture medium is fed from the inducing factor feeder 12 to the space between the first filter and the second filter, and then, the target cells collected in this space in the trap 13 are fed to the establisher 14 together with the fed inducing-factor-containing culture medium.

In this structure, opening and closing mechanisms may be provided for the respective first and second filters to selectively open and close their mesh openings. Such opening and closing mechanisms may have an electrically or mechanically controllable configuration. At the time of feeding the suspension liquid from the suspension liquid feeder 11, the mesh openings of the first filter and the second filter are opened so that substances having a particle size smaller than the first particle size (which is larger than each target cell) pass through the first filter, and the substances having the second particle size equivalent to the size of the target cell are caught while the substances having a particle size smaller than the second particle size pass through the second filter. At the time of feeding the inducing-factor-containing culture medium from the inducing factor feeder 12, the mesh openings of the first filter and the second filter are closed so that the inducing-factor-containing culture medium and the target cells are inhibited from flowing out through the first mesh of the first filter and the second mesh of the second filter, and the inducing-factor-containing culture medium and the target cells are allowed to flow toward the establisher 14.

(Modification 10)

The foregoing embodiment, etc. have assumed that the trap 13 has the filter 131 for catching the target cells. However, the trap 13 may omit the filter 131 as long as the trap 13 is capable of catching the target cells. The iPS cell establishment apparatus 1 according to this Modification 10 includes a controller for controlling the trap 13. At the time of feeding the suspension liquid from the suspension liquid feeder 11, the controller controls the trap 13 to catch the target cells contained in the suspension liquid. Also, at the time of feeding the inducing-factor-containing culture medium from the inducing factor feeder 12, the controller controls the trap 13 to release the target cells. For example, the controller and the trap 13 may be adapted to catch the target cells electrically, magnetically, and/or optically. The controller applies electric energy, magnetic energy, and/or optical energy to the trap 13 so that the trap 13 catches the target cells, and the controller stops the application of the electric energy, magnetic energy, and/or optical energy to the trap 13 so that the trap 13 releases the target cells.

(Modification 11)

The foregoing embodiment, etc. have assumed that the operator or the like makes liquid flow downstream by operating the upstream container which contains the liquid. However, the operator or the like can make the liquid flow downstream by operating the downstream container into which the liquid flows or units connected to the downstream container.

For example, the waste liquid receiver 16 may include an injector, and the suspension liquid feeder 11 may be constituted by a bag. In this configuration, by pulling the piston of the waste liquid receiver 16 with the path from the suspension liquid feeder 11 to the waste liquid receiver 16 formed as in FIG. 3, the operator or the like can perform the operation of step S2.

For example, the waste liquid receiver 16 may include an injector, and the wash liquid feeder 15 may be constituted by a bag. In this configuration, by pulling the piston of the waste liquid receiver 16 with the path from the wash liquid feeder 15 to the waste liquid receiver 16 formed as in FIG. 4, the operator or the like can perform the operation of step S4.

For example, the inducing factor feeder 12 may be constituted by a bag. In this configuration, by pulling the piston of the establisher 14 with the path from the inducing factor feeder 12 to the establisher 14 formed as in FIG. 5, the operator or the like can perform the operation of step S6.

According to at least one of the embodiments, etc. described above, the iPS cell establishment apparatus 1 includes the suspension liquid feeder 11, the trap 13, the inducing factor feeder 12, and the establisher 14. The suspension liquid feeder 11 feeds the suspension liquid containing target cells. The trap 13 traps the target cells contained in the suspension liquid fed from the suspension liquid feeder 11. The inducing factor feeder 12 feeds an inducing factor to the trap 13. The establisher 14 establishes iPS cells by having the inducing factor that has been fed to the trap 13 introduced into the target cells that have been trapped by the trap 13.

According to the above configuration, the collection of the target cells from the suspension liquid can be enabled and the establishment of iPS cells from the collected target cells can be realized without the need for large scale installations such as a centrifugal separator. Also with this configuration, an operator or the like is not required to perform special, skillful work for establishing iPS cells, and therefore, the variations in qualities of the iPS cells can be suppressed. More specifically, the operator or the like is only expected to manipulate the suspension liquid feeder 11, the inducing factor feeder 12, each of the valves 31 to 35, and so on, and such manipulating operations are considered to be easy work without requiring a special skill. The iPS cell establishment apparatus 1 secures its components intended for the processes from the feeding of the suspension liquid until the establishment of iPS cells in an airtight manner against the ambient air, and as such, the iPS cell establishment apparatus 1 assures cleanness. Also, in the iPS cell establishment apparatus 1, the components intended for the processes from the feeding of the suspension liquid until the establishment of iPS cells are integrally constructed, and as such, the target cells can be protected from cross contamination. Moreover, for suspension liquids of more than one origin, a multiple of the iPS cell establishment apparatuses 1 may be employed concurrently and respectively, so that iPS cells of multiple donors can be established at once and the time required for the establishment of the iPS cells can be greatly reduced.

Therefore, the embodiment, etc. described above can realize the simple and advantageous establishment of iPS cells.

The term "processor" used herein refers to, for example, a CPU or a GPU, or various types of circuitry, such as an application-specific integrated circuit (ASIC), a programmable logic device (e.g., a simple programmable logic device (SPLD), a complex programmable logic device (CPLD), or a field programmable gate array (FPGA)), and so on. The processor reads programs stored in storage circuitry and executes them to realize the intended functions. The programs may be incorporated directly in circuits of the processor, instead of being stored in the storage circuitry. According to such architecture, the processor reads the programs incorporated in its circuits and executes them to realize the functions. As another option, functions corresponding to the programs may be realized by a combination of logic circuits, instead of having the programs executed. The embodiment, etc. described herein do not limit each processor to a single circuitry-type processor. Multiple independent circuits may be combined and integrated as one processor to realize the intended functions. Furthermore, multiple components or features may be integrated as one processor to realize the respective functions.

While certain embodiments have been described, they have been presented by way of example only, and are not intended to limit the scope of the inventions. Indeed, the novel embodiments described herein may be embodied in a variety of other forms. Furthermore, various omissions, substitutions, and changes in the form of the embodiments may be made without departing from the spirit of the inventions. The accompanying claims and their equivalents are intended to cover such forms or modifications as would fall within the scope and spirit of the inventions.

The invention claimed is:

1. A method for supplying a mixed liquid containing a mononuclear cell and an inducing factor for inducing reprogramming of the mononuclear cell to a container, the method comprising:
   a first step of sending a suspension liquid containing the mononuclear cell to a trap through a first flow channel in a first direction, the trap configured to trap the mononuclear cell contained in the suspension liquid sent in the first step, the trap being arranged in the first flow channel; and
   a second step of sending the inducing factor to the trap in a second direction opposite the first direction through the first flow channel, and sending the mononuclear cell trapped by the trap and the inducing factor to the container through a second flow channel branching off from the first flow channel at a branch position upstream of the trap in the first direction.

2. The method according to claim 1, wherein the trap comprises a mesh to catch the mononuclear cell, the mesh being configured to catch a substance having a particle size larger than an opening of the mesh and permit a substance having a particle size smaller than the opening to pass through.

3. The method according to claim 1, wherein the trap comprises a first mesh and a second mesh,
   the first mesh being configured to catch a substance having a first particle size larger than the mononuclear cell and permit a substance having a particle size smaller than the first particle size to pass through,
   the second mesh being configured to catch a substance that has passed through the first mesh and has a second particle size equivalent to the mononuclear cell, and permit a substance having a particle size smaller than the second particle size to pass through.

4. The method according to claim 3, wherein the second step sends the inducing factor to a space between the first mesh and the second mesh.

5. The method according to claim 1, further comprising a wash liquid feeding step of sending a wash liquid to the trap, by which a substance other than the mononuclear cell remaining in the trap is washed away.

6. The method according to claim 5, wherein the wash liquid feeding step comprises sending the wash liquid to the trap after the first step sends the suspension liquid and before the second step sends the inducing factor.

7. The method according to claim 5, wherein the wash liquid feeding step comprises repeatedly suctioning and discharging the wash liquid sent to the trap so that the substance other than the mononuclear cell remaining in the trap is washed away.

8. The method according to claim 1, wherein the second step sends, together with the inducing factor, a culture medium.

9. The method according to claim 1, wherein the first step sends blood or a preservative solution as the suspension liquid.

10. The method according to claim 1, further comprising:
sending a preservative solution to the trap, and
recovering the preservative solution containing the mononuclear cell trapped by the trap.

11. A liquid supplying apparatus, comprising:
a suspension liquid feeder configured to send a suspension liquid containing a mononuclear cell through a first flow channel in a first direction:
a trap connected to the suspension liquid feeder via the first flow channel and configured to trap the mononuclear cell contained in the suspension liquid sent through the first flow channel from the suspension liquid feeder, the trap being arranged in the first flow channel; and
an inducing factor feeder, the inducing factor feeder being configured to send an inducing factor for inducing reprogramming of the mononuclear cell to the trap in a second direction opposite the first direction through the first flow channel, and to send a liquid containing the mononuclear cell and the inducing factor to a container, the container being connected to the trap via a second flow channel branching off from the first flow channel at a branch position upstream of the trap in the first direction.

12. The apparatus according to claim 11, wherein the trap comprises a mesh to catch the mononuclear cell, the mesh being configured to catch a substance having a particle size larger than an opening of the mesh and permit a substance having a particle size smaller than the opening to pass through.

13. The apparatus according to claim 11, wherein the trap comprises a first mesh and a second mesh,
the first mesh being configured to catch a substance having a first particle size larger than the mononuclear cell and permit a substance having a particle size smaller than the first particle size to pass through,
the second mesh being configured to catch a substance that has passed through the first mesh and has a second particle size equivalent to the mononuclear cell, and permit a substance having a particle size smaller than the second particle size to pass through.

14. The apparatus according to claim 11, further comprising the first flow channel, into which the suspension liquid is introduced from the suspension liquid feeder and into which the inducing factor is introduced from the inducing factor feeder,
wherein in the first flow channel, the suspension liquid flows in the first direction, and the inducing factor flows in the second direction opposite the first direction, and
the trap is located in the first flow channel.

15. The apparatus according to claim 14, wherein an establisher is connected to the second flow channel so that the mononuclear cell and the inducing factor are sent to the establisher via the second flow channel.

16. The apparatus according to claim 11, further comprising a controller configured to control the trap,
wherein, at a time of feeding the suspension liquid from the suspension liquid feeder, the controller is configured to control the trap to catch the mononuclear cell contained in the suspension liquid, and at a time of feeding the inducing factor from the inducing factor feeder, the controller is configured to control the trap to release the mononuclear cell.

* * * * *